United States Patent [19]

Srivastava

[11] Patent Number: 4,812,577
[45] Date of Patent: Mar. 14, 1989

[54] MERCURIC ACETATE PHENYL MALEIMIDE USEFUL FOR PREPARING RADIOHALOGENATED MALEIMIDES

[75] Inventor: Prem C. Srivastava, Oak Ridge, Tenn.

[73] Assignee: The United States of America as represented by the United States Department of Energy, Washington, D.C.

[21] Appl. No.: 155,440

[22] Filed: Feb. 12, 1988

Related U.S. Application Data

[62] Division of Ser. No. 43,776, Apr. 28, 1987, Pat. No. 4,735,792.

[51] Int. Cl.⁴ .............................. C07D 207/244
[52] U.S. Cl. ........................... 548/404; 548/549
[58] Field of Search ............. 548/549, 404; 206/569

[56] References Cited

U.S. PATENT DOCUMENTS

| 1,034,092 | 7/1912 | Engelmann | 548/404 X |
| 2,087,960 | 7/1937 | Andersen | 548/404 X |
| 3,406,181 | 10/1968 | Wilks | 548/404 |

FOREIGN PATENT DOCUMENTS

203764  12/1986  European Pat. Off. .

Primary Examiner—John F. Terapane
Assistant Examiner—John S. Maples
Attorney, Agent, or Firm—Katherine P. Lovingood; Stephen D. Hamel; Judson R. Hightower

[57] ABSTRACT

A mercuric maleimide is utilized as a pharmaceutical kit for preparing radiohalogenated maleimides.

1 Claim, 2 Drawing Sheets

MERCURIC ACETATE PHENYL MALEIMIDE USEFUL FOR PREPARING RADIOHALOGENATED MALEIMIDES

This invention relates to radiopharmaceuticals for labeling antibodies and more particularly to radioiodinated malemides capable of labeling thiol containing proteins and was developed pursuant to a contract with the U.S. Department of Energy.

This is a division of application Ser. No. 043,776 filed Apr., 28, 1987, now U.S. Pat. No. 4,735,792.

BACKGROUND OF THE INVENTION

Cancer diagnosis and treatment is one of the most difficult problems facing clinical nuclear medicine today. This is due to the malignancy of some types of tumors, that is, their ability to spread to other parts of the body. By the time a primary tumor can be located it may already have metastasized establishing new colonies of tumor cells throughout the system. It is important to be able to locate these new colonies for it is these metastasis which usually prove to be fatal, not the primary tumor. Certain antibodies can be found with their corresponding antigens at the tumor site. If these antibodies could be labeled with a gamma emmitting radionuclide it would allow the use of existing imagining instruments and techniques to trace the location of the new colonies.

Radiolabeling of antibodies with iodine-131 and iodine-123 has been attempted in the past using what is referred to as the Chloramine-T procedure or a modification of this method. It is believed that the phenyl group of the tyrosine residues in the protein contain the radiolabel. Drawbacks of this procedure include substrate exposure to chemicals during radioiodination and the possibility of non-specific radiolabeling and denaturation of the protein resulting in low yields of the radiolabeled antibody. Another major drawback is in vivo deiodination of the antibody and entrapment of free radioiodine in the stomach mucosa and decreased tissue half-life of the radiolabeled antibody. Therefore, there is a need to develop techniques that provide specific radiolabeling of proteins with a minimum of in vivo chemical degradation of the radiopharmaceutical.

SUMMARY OF THE INVENTION

In view of the above need, it is therefore an object of this invention to provide a radiopharmaceutical for labeling proteins that does not interfere with the biological activity of the protein.

A further object of this invention is the Radiolabeling of antibodies that does not interfer with the biological activity of the antibodies.

Another object of this invention is to provide a radiopharmaceutical for labeling blood proteins that reacts with the thiol groups of the protein.

A further object of this invention is to provide an intermediate for preparing radiopharmaceuticals for blood labeling.

An additional object of this invention is to provide a kit that makes utilization of the radiopharmaceutical easy.

Upon further study of the specification and appended claims, further objects and advantages of this invention will become apparent to those skilled in the arts.

These objects have been achieved by providing compounds of a maleimide having a radiohalogenated phenyl at the maleimide nitrogen site with the phenyl being radiohalogenated at the para position. The objects are further achieved by providing a process for making the radiohalogenated maleimide by mixing maleic anhydride with an aniline that has a radiohalogen at the four position in glacial acetic acid thereby forming crystalline product. This crystalline product is separated from the mixture and dried and subsequently mixed with sodium acetate and acetic anhydride and refluxed in benzene to effect the reaction that produces the radiohalogenated maleimide. The final product of the radiohalogenated maleimide is extracted with chloroform and dried. The objects are also achieved by providing a kit for preparing precursors to the radiohalogenated maleimide which comprises a maleimide having a phenyl mercuric acetate at the N position with the phenyl having its mercuric acetate functional group at the para position.

The radiopharmaceuticals of this invention as well as the process for making them provides a valuable addition to the field of antibody and protein labeling. The compounds are easy and inexpensive to make and they also exhibit high specificity and are easy to detect using conventional imaging techniques. One particular advantage is that they bind to thiol sites which are ordinarily found in proteins but are not necessarily required for biological activity thereby allowing the protein to be labeled and studied with its activity unimpaired.

DETAILED DESCRIPTION OF THE PREFERRED EMBODIMENT

Figure 1:
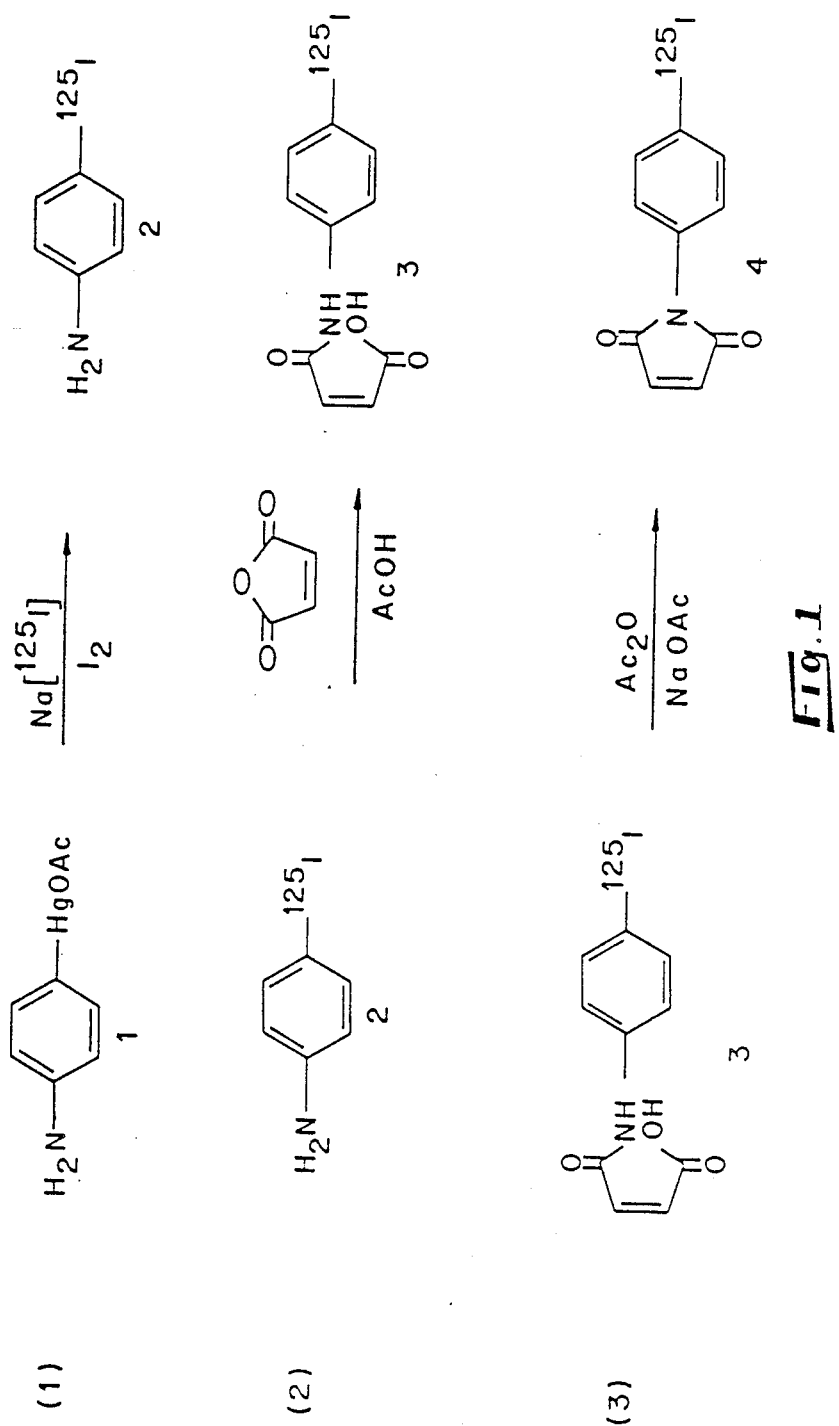
FIG. 1 is the reaction equations for the process of Example 1.

Previously protein labeling has been difficult when utilizing radiopharmaceuticals that react with nitrogen, which is often the active site of proteins. The new radiopharmaceuticals of this invention take advantage of the thiol-seeking properties of maleimides, that is, the tendancy to bind at the sulphur site, thereby freeing up the nitrogen site for further reaction. Maleimides have been previously used for studies of insulin in rat antibodies because of there thiol-seeking characteristics.

Another desirable characteristic of the radiopharmaceutical would be a stabilized radiolabel to prevent in vivo chemical decomposition that would remove the radiolabel from th.e labeling compound. In the past radiohalogens have been studied for protein and methods to stabilize the radiohalogens have been found; specifically, the attachment of a radiohalogen to an unsaturated carbon such as a vinyl group or a phenyl group increases the stability of the halogen on the compound.

Therefore, a radiohalogen, such as iodine, bromine or fluorine, bound to an unsaturated carbon, such as a vinyl or phenyl, attached to a maleimide would be a theoretically suitable compound for labeling blood proteins, since it should attach the protein without disturbing its biological activity and hold the radiolabel on the compound during the process of radioimaging. The compounds of this invention do precisely that. The radiohalogenated maleimides can be made by mixing maleic anhydride and a radiohalogenated aniline and subsequently mixing the product of that reaction with sodium acetate and acetic anhydride and refluxing in bezene to form the radiohalogenated maleimide. The radiohalogen can be made by persons of ordinary skill in tne art. The radiopharmaceutical would have the following structure:

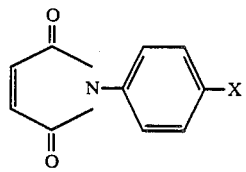

with X being the radiohalogen.

The specific radiolabeled maleimide that has been prepared by the inventors is a radioiodide since the iodine product is most suitable for single photon emission computerized tomography that detects gamma radiation emmitted by the radioiodine.

A kit for preparing the radioiodinated maleimide is also provided so that the reaction time in radiation decay can be minimized when utilizing the radiopharmaceutical in a therapeutic or institutional setting. The kit provides an intact molecule having a functional group that is readily substituted by a radioiodine or other radiohalogen to yield the desired product immediately prior to administration. It is a crystalline compound stable at room temperature and suitable for shipment to locations where it is needed for easy radiolabeling in good yield. The kit can also be used for radiolabeling with relatively short lived I-123 and I-131 radioisotopes. Should metallic radioisotopes be desired it would be possible to use other chelating functional groups to be subjected to similar substitution reactions.

Compounds of this invention can be used for antibody labeling for use in warm blooded animals such as mammals including humans. Administration can be by way of formation of the radiolabeled antibody by mixing the radiolabeled maleimide with the antibody and introduction of the antibody into the system in its radio-iodinated state. Generally, this would be done by mixing the antibody with the radiohalogenated maleimide in a buffer and a solvent such as DMSO and extracting the unbound radioactive compound with ethyl ether and injecting the radiohalogenated antibody into the system.

If blood is to be labeled, either the above procedure can be used by first labeling a blood sample before injecting it into the body or by administering the radiohalogenated maleimide directly into the system of the mammal since tissue distributions studies in rats indicate preferential binding with the blood and the red blood cells. The actual preferred amounts of the active compound in a specific case sufficient to provide a distinct image will vary depending on a number of factors and can be determined using conventional considerations by one of ordinary skill in the art.

A maleimide that was prepared, N-(p-[$^{125}$I] iodophenyl) maleimide (IPM) 4 can be made by a simple, straight forward route as shown in FIG. 1. Iodine is stabalizied on the phenyl ring to inhibit in vivo deiodination.

The maleimide agent, after tissue distribution studies in rats indicated preferential binding with the blood. The low thyroid uptake was indicative of invivo stability of the radiolabel. The agent also appears to bind with IgG, albuim and platelet proteins based on preliminary studies.

EXAMPLE 1

Referring to FIG. 1, Step 1 for the preparation of 4-[$^{125}$I] iodoaniline 2 is described as follows. A commercial sample of iodine-125 (21.8 mCi) received in 0.1N NaOH was first neutralized with a hydrofluoric acid (HF) solution diluted with methanol. A solution of iodine (one atom equivalent of the substrate) in methanol (2 ml) was added to the radioiodide solution to dilute radioactivity. The resulting solution was added to a cooled stirred suspension of finely powdered 4-aminophenylmercuric acetate in methanol. An instantaneous reaction with loss of iodine color was observed. The reaction mixture was stirred for 30 minutes, diluted with water (25 ml) and extracted with ethyl ether. The ether portion was washed with 10 percent aqueous sodium bisulfite solution followed by water and dried. Evaporation of ether followed by silica gel column chromatography provided 4-[$^{125}$I] iodoaniline in 73 percent radiochemical yield.

In step 2, maleic anhydride (95 mg, 1 mmol) and 4-iodoaniline (219 mg, 1 mmol) were stirred in glacial acetic acid (2.5 ml). The separated crystalline product was collected by filtration, washed with water and dried. The air dried material was triturated with dichloromethane, filtered and dried to yield 3: 225 mg (71%), mp 198°–199° C. (decomposition with evolution of iodine).

Analysis calculated for $C_{10}H_8INO_3$: C, 37.88; H, 2.52; N, 4.42; Found: C, 37.85; H, 2.61; N, 4.57.

In step 3, a mixture of 3 (158 mg. 0.5 mmol), sodium acetate (23 mg, 0.28 mmol) and acetic anhydride (150 mg, 1.5 mol) in benzene (2.5 ml) was refluxed. After completion of the reaction, the mixture was passed through a column of silica gel packed in chloroform. The column was eluted with chloroform. The chloroform fractions containing product were evaporated and triturated with carbon tetrachloride and hexane to yield (115 mg, 77%) of 4: mp 159°–161° C.

Analysis calculated for $C_{10}H_6INO_2$: C, 40.16; H, 2.02; N, 4.68; I, 42.43. Found: C, 39.89; H, 2.00; N, 4.43; I, 42.39.

EXAMPLE 2

4-[$_{125}$I] iodoaniline (7.4 mCi sp. act. 700 mCi/mmol) prepared following procedure described in Step 1 of Example 1 was coupled with maleic anhydride (9.5 mg) in glacial acetic acid (0.15 ml) at room temperature. The radioiodinated compound, [$^{125}$I]3 isolated by silica gel column chromatography was refluxed with acetic anhydride (75 mg) and anhydrous (fused) sodium acetate (12 mg) in benzene (1.0 ml) for 3 h.

TABLE

| | The distribution of radioactivity in tisssues of femal Fischer 344 rats after intravenous administration of [$^{125}$I]4.[a] | | | | | |
|---|---|---|---|---|---|---|
| Time after Injection | Mean percent injected dose/gm (range) Tissue | | | | | |
| | Blood | Liver | Kidneys | Heart | Lungs | Thyroid |
| 5 min | 8.84 | 1.90 | 2.15 | 1.45 | 2.04 | 13.66 |

TABLE -continued

The distribution of radioactivity in tisssues of femal Fischer 344 rats after intravenous administration of $[^{125}I]4.^a$

| Time after Injection | Mean percent injected dose/gm (range) Tissue | | | | | |
|---|---|---|---|---|---|---|
| | Blood | Liver | Kidneys | Heart | Lungs | Thyroid |
| 30 min | (7.98–9.51) 8.44 | (1.60–2.59) 1.73 | (1.67–2.52) 2.12 | (1.16–1.83) 1.81 | (0.90–2.77) 2.52 | (8.93–17.64) 21.73 |
| 60 min | (7.87–9.13) 7.56 | (1.47–2.11) 1.50 | 1.62–2.49) 2.07 | (1.43–2.42) 1.74 | (1.90–3.00) 2.31 | (15.5–25.64) 20.49 |
| | (7.22–7.75) | (1.42–1.65) | (1.75–2.40) | (1.41–1.70) | (2.19–2.47) | (14.69–28.51) |

$^a$Animals had body weight range of 121-139 gm. Each animal received 3.7 $^0$Ci of $[^{125}I]4$ by tail vein injection.

TABLE 2

The distribution of radioactivity in tisssues of femal Fischer 344 rats after intravenous administration of $[^{125}I]4.^a$

| Time after Injection | Mean percent injected dose/gm (range) Tissue | | | | | |
|---|---|---|---|---|---|---|
| | Blood | Liver | Kidneys | Heart | Lungs | Thyroid |
| 5 min | 57.58 (55.49–59.64) | 10.16 (7.79–15.82) | 2.17 (1.84–2.67) | 0.61 (0.44–0.86) | 1.76 (1.46–2.28) | 0.13 (0.09–0.17) |
| 30 min | 54.07 (51.53–57.21) | 7.85 (7.06–9.27) | 2.18 (1.70–2.74) | 0.79 (0.64–1.02) | 1.89 (1.32–2.36) | 0.20 (0.15–0.25) |
| 60 min | 48.56 (46.22–50.76) | 7.05 (6.04–7.93) | 2.21 (1.91–2.61) | 0.74 (0.61–0.85) | 1.74 (1.62–1.85) | 0.19 (0.15–0.28) |

$^a$Animals had body weight range of 121-139 gm. Each animal received 3.7 $^0$Ci of $[^{125}I]4$ by tail vein injection.

The product, $[^{125}I]4$ (3.99 mCi, 56 percent radiochemical yield based on $[^{125}I]3$), was isolated by silica gel column chromatography. The radioactive compound $[^{125}I]4$ was identical with an unlabeled sample of 4.

Rats were injected with $[^{125}I]4$ and the uptake of radioactivity in different tissues is given in Table 1 and Table 2.

The data demonstrated that high levels of radioactivity were associated with the blood. Blood fractionation (plasma, red and white blood cells) studies indicated 88.9% of the blood activity to be associated with red blood cells. These studies demonstrate that $[^{125}I]4$ can be used for labeling for red blood cells for use as diagnostic radiopharmaceuticals.

EXAMPLE 3

Samples of bovine albumin (45 mg/ml, 10 ml) and human γglobulin (6.7 mg/ml. 10 ml) were prepared in phosphate buffer and 0.15 NaCl solution (PBS). A 10 ml sample of PBS was used as control. $[^{125}I]$-IPM (10 μCi) in 100 λDMSO was added to each sample and incubated for 30 min at 37° C. The samples were repeatedly extracted with ethyl ether. The unbound activity as $[^{125}I]$-IPM was extracted with ethyl ether. The activity remaining in the aqueous portion was considered to be bound with the proteins. Almost all of the activity was recovered in ether from the control sample. γglobulin and albumin samples showed ~40 percent and ~60 percent activity, respectively, remaining in the aqueous portions. TLC analyses of these aqueous portions showed the radioactivity to be associated with a polar band indicating significant binding of $[^{125}I]$-IPM with these proteins. These studies demonstrate that $[^{125}I]$-IPM can be used for labeling antibodies.

EXAMPLE 4

Figure 2:
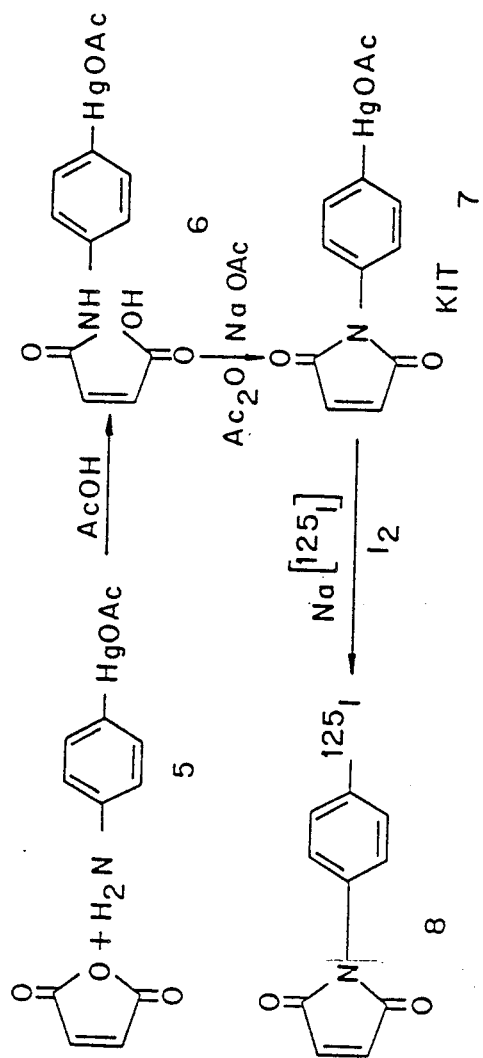
FIG. 2 is the reaction equations for making the kit of Example 4.

The compound of the kit was prepared as diagramed in FIG. 2.

Maleic anhydride (95 mg, 1 mmol) and p-aminophenyl mercuric acetate 5 (351 mg, 1 mmol) were disolved in glacial acetic acid (1 ml and 2 ml, respectively). These solutions were combined and stirred for 30 min. The yellow precipitate formed was collected using suction filtration and washed with glacial acetic acid. The precipitate was stirred with acetone and recollected using a Buchner funnel. The product 6 was dried overnight under vacuum with sodium hydroxide pellets. This reaction was performed to yield 350 mg (70%) of pure (6) mp 177–179; $^1$H NMR (dimethyl sulfoxide-d$_6$) 2.2 (s, 3H, OCH$_3$), 4.0 (broad peak, 1H, N—H) 6.6 (s, 1H, carboxylic H); Elemental Analysis: %C 32.17, %H 2.61, %N 3.07, %Hg 44.08.

A mixture of 6 (970 mg, 2 mmol) and fused sodium acetate (46 mg, 0.56 mmol) in acetic anhydride (2 ml) and benzene (10 ml) was refluxed with stirring for 3 h. The precipitate formed during the reaction was filtered with a Buchner funnel and washed with benzene. The mother-liquor was pored over ice (15 ml), at which point a precipitate was formed. The precipitate and solution were transferred to a separatory funnel and extracted with ethyl ether (3×20 ml). The ether fractions were combined and washed with water (1×20 ml). The ether layer was then dried with sodium sulfate. Upon evaporation and coevaporation with carbon tetrachloride, a yellow participate was formed. The solid was collected by filtration and dried overnight under vacuum with sodium hydroxide pellets to yield 316 mg (37%) of N-(p-Acetylmercuricphenyl) maleimide 7; mp 147–149; $^1$H NMR (deutarated chloroform) 2.2 (s, 3H, OCH$_3$), 6.9 (s, 2H, maleimide H), 7.5 (s. 2H, maleimide H), 7.5 (s, 4H, aromatic H). The compound 7 comprises the kit and is easily converted to the radiopharmaceutical 8 by radioiodination following the procedure described in Example 1, Step 1.

This maleimide agent shows interesting properties as a potential protein labeling agent. It can be prepared in high specific activity, and tissue studies in rats indicate preferential binding of IPM with the blood. In addition, consistently low thyroid levels of radioactivity indicate the stability of the maleimide agent toward in vivo deiodination. The agent also appears to bind with IgG, albumin and platelet proteins based on preliminary studies. Its tendancy to bind to thiol groups is significant and in the absence of a naturally occurring thiol group one can be easily added by persons of ordinary skill in the art to achieve the same result.

The kit described in this patent application provides a very simple and inexpensive method easily available to institutions that desire to label proteins using this radiopharmaceutical.

I claim:

1. A compound for use in a radiopharmaceutical kit for preparing radiohalogenated maleimides consisting of a maleimide having a mercuric acetate phenyl at the N. position, said phenyl having its mercuric acetate functional group at the para-position.

* * * * *